United States Patent [19]

Relyea et al.

[11] Patent Number: 5,061,716
[45] Date of Patent: Oct. 29, 1991

[54] FUNGICIDAL 3,3-BISTHIOALKYL-2-PYRIDYLACRYLIC ACID COMPOUNDS

[75] Inventors: Douglas I. Relyea, Bethany; Robert A. Davis, Cheshire, both of Conn.

[73] Assignee: Uniroyal Chemical Company, Inc., Middlebury, Conn.

[21] Appl. No.: 582,295

[22] Filed: Sep. 13, 1990

[51] Int. Cl.$^5$ .................. A61K 31/44; C07D 213/30
[52] U.S. Cl. .................. 514/336; 546/270; 546/283; 546/341; 546/342; 514/338; 514/277
[58] Field of Search .............. 546/341, 342, 270, 283; 514/277, 336, 338

[56] References Cited

U.S. PATENT DOCUMENTS 3,407,186 10/1968 Haas et al. ..................... 546/341

FOREIGN PATENT DOCUMENTS 0041664 3/1985 Japan ..................... 546/341
0087570 4/1987 Japan ..................... 546/341

OTHER PUBLICATIONS

Chemical Abstracts, vol. 88, No. 1, Abstract 6669p, p. 566, Jan. 2, 1978.

Primary Examiner—C. Warren Ivy
Assistant Examiner—Zinna Northington-Davis
Attorney, Agent, or Firm—Glenn E. Karta

[57] ABSTRACT

Compounds having the structure

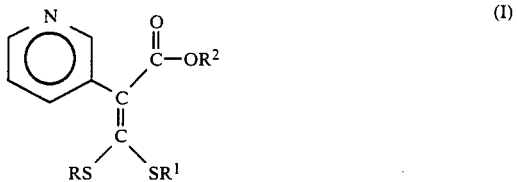

wherein:
R and $R^1$ are each independently members selected from the group consisting of
  $C_1$-$C_{10}$ alkyl,
  $C_1$-$C_{10}$ cyanoalkyl,
  $C_7$-$C_{13}$ arylalkyl,
  $C_2$-$C_9$ alkenyl,
  $C_3$-$C_9$ haloalkenyl
  $C_3$-$C_{10}$ alkoxyalkyl,
  $C_3$-$C_{10}$ alkylthioalkyl,
  $C_3$-$C_{10}$ alkylsulfonylalkyl,
  $C_3$-$C_8$ carbalkoxyalkyl,
  $C_4$-$C_{10}$ alkylenedioxyalkyl,
  $C_7$-$C_{13}$ aryloxyalkyl, and
  $C_5$-$C_8$ alkenyloxyalkyl; and
$R^2$ is $C_1$-$C_5$ alkyl, are disclosed which have fungicidal activity. Fungicidal compositions comprising the compounds and a carrier are also disclosed, as are methods for controlling the growth of phytopathogenic fungi utilizing the compounds. Methods for the preparation of such compounds are also disclosed.

15 Claims, No Drawings

FUNGICIDAL 3,3-BISTHIOALKYL-2-PYRIDYLACRYLIC ACID COMPOUNDS

BACKGROUND OF THE INVENTION

1. Field of the Invention

The present invention is directed to a new class of 3,3-bisthioalkyl-2-pyridylacrylic acid derivatives, particularly the esters, which are useful as fungicides.

The control of phytopathogenic fungi is of great economic importance since fungal growth on plants or on parts of plants such as fruits, blossoms, foliage, stems, tubers, roots and the like not only inhibits production of a plant as well as commercially significant portions thereof, its foliage, fruit and seed, but, in addition, reduces the overall quality of the harvested crop.

To overcome or at least reduce the detrimental effects of fungi, plants have long been treated with fungicides. However, the enormous economic toll taken by identified fungi, as well as the development of new fungus strains resistant to known fungicides, establishes a continuing need to develop new and more effective fungicides which possess curative, preventative and systemic action to protect cultivated plants. These new fungicides must not only possess these protective properties, they must not possess properties which have an adverse effect on the plants to be protected.

2. Description of Related Art

U.S. Pat. No. 3,761,596 is directed to a class of fungicidal compositions containing malonic esters, including the commercial fungicide Isoprothiolane (di-isopropyl 1,3-dithiolane-2ylidenemalonate):

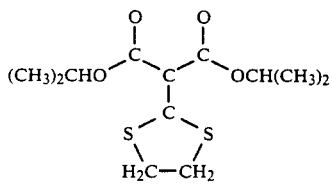

Compound (A) is for practical purposes a "one-species" fungicide, being effective at economic rates only against *Pyricularia oryzae*, the causative organism of rice blast. In contrast, the compounds of the present invention are active against a broad spectrum of Phytopathogenic organisms.

SUMMARY OF THE INVENTION

One aspect of the present invention is a new class of compounds having the structural formula

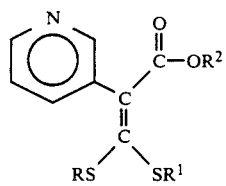

and stereoisomers thereof, wherein:

R and $R^1$ are each independently members selected from the group consisting of
$C_1$–$C_{10}$ alkyl,
$C_1$–$C_{10}$ cyanoalkyl,
$C_7$–$C_{13}$ arylalkyl,
$C_2$–$C_9$ alkenyl,
$C_3$–$C_9$ haloalkenyl
$C_3$–$C_{10}$ alkoxyalkyl,
$C_3$–$C_{10}$ alkylthioalkyl,
$C_3$–$C_{10}$ alkylsulfonylalkyl,
$C_3$–$C_8$ carbalkoxyalkyl,
$C_4$–$C_{10}$ alkylenedioxyalkyl,
$C_7$–$C_{13}$ aryloxyalkyl, and
$C_5$–$C_8$ alkenyloxyalkyl; and
$R^2$ is $C_1$–$C_5$ alkyl.

The present invention is also directed to fungicidal compositions comprising (A) a fungicidally effective amount of at least one compound having structure (I) above, and (B) an agriculturally acceptable carrier. Further, the present invention is directed to a process for controlling undesirable fungi comprising applying a fungicidally effective amount of at least one compound or composition of the present invention to loci to be protected. The present invention is also directed to methods for the preparation of the compounds of this invention.

DETAILED DESCRIPTION OF THE INVENTION

The compounds of the present invention may be prepared by reacting an alkyl 3-pyridylacetate having the structural formula

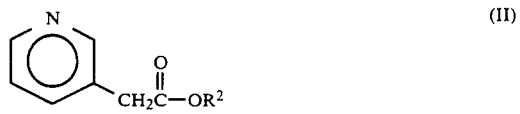

wherein $R^2$ is as defined above, with carbon disulfide in the presence of a base such as potassium hydroxide in a polar solvent, preferably dimethyl sulfoxide. The reaction occurs at room temperature over a period of from 6–18 hours. Following that reaction, an appropriate alkyl halide is added, having the structural formula

RX or $R^1$X    (III)

where R and $R^1$ are as defined above and X is halogen, preferably chlorine or especially bromine If R and $R^1$ are different, the products are made by successive alkylations of the two sulfur atoms with different reagents. The first alkylation is with the less reactive reagent, using the more reactive reagent in the last, more sterically hindered reaction. The alkylation is carried out at room temperature with a small exotherm occurring during the addition of the alkyl halide.

The preferred stoichiometric ratio of the reactants which results in the formation of the desired compound having the structural formula I is one molar equivalent of the alkyl 3-pyridylacetate having the structural formula II to a slight excess of one molar equivalent of carbon disulfide and two molar equivalents of the alkyl halide having the structural formula III.

The desired compound (formula I) is isolated by pouring into water, extracting with several portions of chloroform, subsequent evaporation of the chloroform, chromatography on alumina, eluting with chloroform and finally evaporation of the chloroform.

More preferably, the compounds in this invention have structures represented by formula (I) and stereoisomers thereof, where R and $R^1$ are each independently a substituent or group of substituents representing $C_1$–$C_{10}$ alkyl; benzyl; 4-chlorobenzyl; 4-methoxybenzyl; 4-t-butylbenzyl; 3,4-dimethylbenzyl; 3,4,5-trimethoxybenzyl; 3,4-methylenedioxybenzyl; 2-vinyloxyethyl; 2,2-dimethoxyethyl; 2-methoxyethyl; 2-(methylthio)ethyl; 2-(1,3-dioxolan-2-yl)ethyl; 2-(1,3-dioxan-2-yl)ethyl; carboethoxymethyl; 2-carboethoxyethyl; 2-cyanoethyl; 3-phenoxypropyl; 3-(4-t-butylphenoxy)propyl; 2-methylallyl; 3,3-dimethylallyl; but-3-en-1-yl; 3,7-dimethyloct-6-en-1-yl; 2-chloroallyl or 3-chloroallyl; and $R^2$ is methyl, ethyl, isopropyl or n-pentyl. Preferred is $R+R^1$ equals a total of 6 to 9 non-hydrogen atoms and at least one of $R+R^1$ containing a C-C double bond. Less preferred are compounds in which the two sulfur atoms are placed in a ring, i.e., $R+R^1$ equals alkylene, as those compounds are generally less active than compounds in which the two sulfur atoms are not in a ring.

Particularly preferred compounds include:

ethyl 3,3-bis(allylthio)-2-(3-pyridyl)-acrylate;

cis+trans, ethyl 3-allylthio-3-benzylthio-2-(3-pyridyl)acrylate;

ethyl 3,3-bis(2-methyl-2-propenylthio)-2-(3-pyridyl)acrylate;

cis+trans, ethyl 3-(allylthio)-3-(3-phenoxypropylthio)-2-(3-pyridyl)acrylate;

cis+trans, ethyl 3-(allylthio-3-(3,7-dimethyloct-6-en-1-yl-thio)-2-(3-pyridyl)acrylate;

cis+trans, ethyl 3-allylthio-3-[2-(1,3-dioxolan-2-yl)ethylthio]-2-(3-pyridyl) acrylate;

cis+trans, ethyl 3-allylthio-3-(2-methoxyethylthio)-2-(3-pyridyl)acrylate:

cis+trans, ethyl 3-allylthio-3-(4-methoxybenzylthio)-2-(3-pyridyl)acrylate and cis+trans, ethyl 3-allylthio-3-(1,3-benzodioxol-5-yl-methylthio)-2-(3-pyridyl)acrylate.

The fungicidal composition of the present invention comprises a fungicidally effective amount of at least one compound having the structural formula I as an active ingredient and an acceptable carrier therefor. Preferred compositions include at least one preferred compound described above.

The composition of the present invention includes, as one component thereof, a carrier suitable for admixture with the active ingredient. Any appropriate carrier known to the artisan is suitable. The carrier may be solid, for example, finely divided particulate solids, granules, pellets, wettable powders, soluble powders and the like. Among the solid carriers within the contemplation of the subject invention are organic and inorganic materials such as attapulgite clay, sand, vermiculite, corncob, activated carbon and mineral silicates. Among the mineral silicates preferred for use in the composition of the present invention are mica, talc, pyrophyllite, clays and the like.

A solid composition may be prepared from a solid carrier, such as one of those described immediately above. In that case, the active compound is impregnated onto the solid carrier. Alternatively, the active compound may be formulated into a wettable powder by grinding it into a fine powder and mixing it with the solid carrier to which a surface active dispersing agent has been added. The wettable powder is then dispersed in water and applied as a dispersion.

Indeed, the above described dispersion is representative of a composition which may also be classified as a liquid composition. In addition to liquid dispersions, the liquid composition may be in the form of a solution or an emulsion. The case of a liquid solution, the active ingredient is dissolved in an aqueous or organic solvent. In most cases the solvent, which acts as the carrier, is organic. In addition to aromatic hydrocarbons, such a toluene and xylene, other preferred solvents include such organic compounds as acetone, methanol, isopropanol, t-butyl alcohol, cyclohexanone, dioxane, dimethylformamide, dimethyl sulfoxide; ethylene dichloride, diacetone alcohol and N-methylpyrrolidone.

A water emulsion, another preferred embodiment of a liquid composition within the contemplation of the present invention, is prepared from a solution, as described above, to which a surface active agent is added. Surface active agents suitable for use in forming an emulsion within the contemplation of this invention are known to those skilled in the art. McCutcheon's Detergents and Emulsifiers, Allured Publishing Corp., Ridgewood, N.J. (1970); U.S. Pat. No. 2,514,916, at columns 2 to 4; and U.S. Pat. No. 2,547,734, at columns 3 and 4, provide detailed examples of such surface active agents suitable for this purpose. As indicated in these references, the surface active agent may be anionic, non-ionic or cationic.

The carrier component of the present composition may also be an aerosol. To prepare an aerosol, the active compound is dissolved in a non-highly volatile solvent. This solution is then admixed with a highly volatile solvent, a so-called liquid aerosol carrier The aerosol carrier is liquid only under elevated pressure. At ambient temperature and pressure, the aerosol carrier is a gas. In a subembodiment of this preferred carrier, the aerosol carrier may itself be active. For example, the carrier may be an insecticide, a herbicide, a bacteriacide or the like.

The compounds and compositions of the present invention may be used in methods for controlling phytopathogenic fungi. In those methods, a fungicidally effective amount of the active ingredient, whether in compound or composition form, is applied to the locus under attack by fungi.

In one preferred embodiment, the active ingredient is applied to the locus under attack by the fungi by application to the foliage of the plants to be protected. This so-called "foliar treatment" is effectuated by applying the active ingredient to the foliage at a concentration of between about 10 and about 500 milligrams per liter of inert liquid in which the compound is disposed to the foliage of the plants to be protected.

In another preferred embodiment, a fungicidally effective amount of the active ingredient is applied to the soil in which the plants to be protected are grown. In this method, the so-called "systemic treatment," the active ingredient is applied to the soil in which the plant to be protected is grown in a concentration of between abut 0.125 and about 10 kilograms per hectare (kg/ha) of soil. More preferably, systemic control involves application of between about 1.125 kg/ha to about 5 kg/ha.

Independent of which preferred embodiment of controlling fungi is utilized, either the foliar or systemic treatment, the active ingredient may be applied prior to or after infection by fungi. Furthermore, it should be appreciated that the exact dosage, applied systemically or to the foliage, is dictated by the fungus to be controlled and the particular plant to be protected.

In still another embodiment of the present invention, the active ingredient is applied as a coating to the seeds of the plant to be protected. The fungicidal coating protects the soil from the infection by the fungi and is also taken up the plant systemically to protect the plant from fungal attack. In this so-called "seed coating method," an appropriate concentration of the active ingredient is in the range of between about 5 and 75 grams per hundred kilograms of seed.

The following examples are given to illustrate the present invention. Because these examples are given for illustrative purposes only, these examples should not be interpreted as limiting the invention to the scope of the examples recited hereinafter.

EXAMPLE 1

Preparation of ethyl 3,3-bis(allylthio)-2-(3-pyridyl) acrylate (Compound No. 4)

In a three-necked 250 ml flask equipped with magnetic stirrer, thermometer, and reflux condenser with drying tube were placed 5.78 grams (35.0 mmoles) ethyl 3-pyridylacetate, 4.95 grams (88.2 mmoles) powdered reagent potassium hydroxide, 75 ml HPLC-grade dimethyl sulfoxide, and 2.66 grams (35.0 mmoles) reagent carbon disulfide. The mixture was stirred at room temperature for 6.25 hours, during which most of the potassium hydroxide dissolved.

Allyl bromide (8.47 grams, 70.0 mmoles) was added during ninety minutes in four approximately equal portions. The reaction mixture was stirred at room temperature overnight and then poured into 1600 ml of water. The mixture was extracted with three 35-ml portions of chloroform. The chloroform extracts were combined and washed with two 1500-ml portions of water. Evaporation of the chloroform gave 9.4 grams of oily brown crude product. Chromatography on 152 grams of Brockmann grade 1 alumina eluting with chloroform gave a 250-ml fraction of $R_f$ 1.0 to 0.4. Evaporation gave 5.8 (52%) of yellow-orange oil.

The compound was identified by its nuclear magnetic resonance data which was as follows: NMR (CDCl$_3$) $\sigma$:t(3)1.1–1.3; m(2)3.3–3.5; q(4)3.7–4.4; m(4)4.7–5.3; m(2)5.5–6.0; m(1)7.0–7.3; m(1)7.5–7.9; m(2)8.5–8.7.

EXAMPLE 2

Preparation of cis+trans ethyl 3-allylthio-3-benzyl thio-2-(3-pyridyl)acrylate (Compound No. 8)

In a 250-ml three-necked flask equipped with magnetic stirrer, thermometer, and reflux condenser with drying tube were placed 2.15 grams (13.0 mmoles) ethyl 3-pyridylacetate, 28 ml HPLC-grade dimethyl sulfoxide, 1.68 grams (30.0 mmoles) powdered reagent potassium hydroxide and 0.99 grams (13.0 mmoles) reagent carbon disulfide. The mixture was stirred overnight at room temperature. A red color developed and most of the potassium hydroxide dissolved.

In single portions were added 2.22 grams (13.0 mmoles) of benzyl bromide and eighty minutes later 1.57 grams (13.0 mmoles) of allyl bromide. In the first alkylation there was an exotherm from 22.3° C. to 33.0° C.; in the second alkylation an exotherm from 22.8° C. to 26.4° C. The reaction mixture was stirred seventy hours at room temperature and then worked up by quenching in water (1800 ml) and extracting with chloroform (4×30 ml). The combined extracts were washed with water (2×1500 ml) and evaporated down to give 2.9 grams of crude product. Chromatography on Brockmann grade 1 alumina eluted with chloroform gave 1.5 grams of pure product (31% yield). Thin-layer chromatography on silica eluted with 5% methanol in methylene chloride gave a single spot, but the NMR spectrum, consistent with the structure above, shows two triplets for the methyl group. Hence there are cis and trans isomers with some methyl near a benzyl and other methyl near an allyl. The complete NMR spectrum was as follows: NMR (CDCl$_3$)$\sigma$: t,t(3)1.0–1.4; m(4)3.3–4.0; m(2)4.0–4.2; m(2)4.8–5.4; m(1)5.5–6.0; m(6)7.0–7.4; m(1)7.4–7.9; m(2)8.3–8.8.

EXAMPLE 3

Preparation of 2-(alpha-(3-pyridyl)-alpha-carboethoxy) methylidene 1,3-dithiolane (Compound No. 1)

In a 250-ml three-necked flask equipped with magnetic stirrer, thermometer, and reflux condenser with drying tube were placed 12.6 grams (225 mmoles) of reagent potassium hydroxide, 150 ml reagent dimethyl sulfoxide, 16.52 grams (100 mmoles) of ethyl 3-pyridylacetate and 7.60 grams (100 mmoles) of reagent carbon disulfide.

The mixture was stirred without heating for 3.5 hours. The maximum temperature, attained after one hour, was 34.5° C.

Ethylene dibromide (18.8 grams, 100 mmols) was added in three portions over 70 minutes. The maximum temperature was 37° C. The reaction mixture was stirred for sixteen hours without heating and then poured into 1600 ml of water. The mixture was extracted with three 40-ml portions of chloroform. The chloroform was removed with a rotary evaporator to give an oily residue of 23 grams. The residue was chromatographed on 340 grams of activated alumina, eluting with chloroform and collecting one fraction of $R_f$1.0 to 0.4. Evaporation of the chloroform gave 15.1 (59.1%) of a yellow solid identified by its proton NMR spectrum which was as follows: NMR (CDCl$_3$)$\sigma$: t(3)1.05–1.3; m(4)3.1–3.7; q(2)3.9–4.3; m(2)7.1–7.7; m(2)8.5.

EXAMPLE 4

Preparation of Compounds 2-3, 5-7 and 9-52

Additional compounds were prepared in accordance with the procedures enumerated in Examples 1, 2 and 3. These compounds are summarized in Table I, which appears below and their characterizing NMR data appear in Table II. For convenience, the equivalent data for Compounds Nos. 1, 4 and 8, formed in accordance with Examples 3, 1 and 2, respectively, are also included in Tables I and II.

TABLE I $$\underset{RS}{\overset{N}{\bigcirc}}\overset{\overset{O}{\parallel}}{\underset{C}{C}}-OR^2$$

| Cpd. No. | R | R¹ | R² |
|---|---|---|---|
| 1 | —C₂H₄— | | C₂H₅ |
| 2 | —CH(C₆H₄)CH₂— | | C₂H₅ |
| 3 | C₆H₅CH₂ | C₆H₅CH₂ | CH₃ |
| 4 | CH₂=CHCH₂ | CH₂=CHCH₂ | C₂H₅ |
| 5 | C₆H₅CH₂ | C₆H₅CH₂ | C₂H₅ |
| 6 | C₄H₉ | C₄H₉ | C₂H₅ |
| 7 | CH₃ | CH₂C(O)OC₂H₅ | C₂H₅ |
| 8 | C₆H₅CH₂ | H₂C=CHCH₂ | C₂H₅ |
| 9 | n-C₅H₁₂ | n-C₅H₁₂ | C₂H₅ |
| 10 | n-C₃H₇ | n-C₃H₇ | C₂H₅ |
| 11 | n-C₆H₁₃ | n-C₆H₁₃ | C₂H₅ |
| 12 | C₂H₅ | C₂H₅ | C₂H₅ |
| 13 | CH₂=CHCH₂CH₂ | CH₂=CHCH₂CH₂ | C₂H₅ |
| 14 | CH₂=C(CH₃)CH₂ | CH₂=C(CH₃)CH₂ | C₂H₅ |
| 15 | CH₃ | 4-Cl-C₆H₄-CH₂ | C₂H₅ |
| 16 | n-C₁₀H₂₁ | CH₂=CHCH₂ | C₂H₅ |
| 17 | (CH₃)₂CHCH₂ | (CH₃)₂CHCH₂ | C₂H₅ |
| 18 | CH₂=CHCH₂ | 4-(CH₃)₃C-C₆H₄-CH₂ | C₂H₅ |
| 19 | CH₂=C(Cl)CH₂ | CH₂=C(Cl)CH₂ | C₂H₅ |
| 20 | ClCH=CHCH₂ | ClCH=CHCH₂ | C₂H₅ |
| 21 | CH₂=CHCH₂ | (CH₃)(n-C₆H₁₃)CH | C₂H₅ |
| 22 | CH₂=CHCH₂ | C₆H₅-OCH₂CH₂CH₂ | C₂H₅ |
| 23 | CH₂=CHCH₂ | 4-(CH₃)₃C-C₆H₄-OCH₂CH₂CH₂ | C₂H₅ |
| 24 | (CH₃)₂C=CHCH₂ | (CH₃)₂C=CHCH₂ | C₂H₅ |
| 25 | CH₃ | CH₂=CH(CH₂)₆ | C₂H₅ |
| 26 | CH₂=C(CH₃)CH₂ | CH₂=C(CH₃)CH₂ | n-C₅H₁₁ |
| 27 | CH₂=CHCH₂ | CH₂=CHCH₂ | C₂H₅ |
| 28 | CH₂=CHCH₂ | CH₂=CHOCH₂CH₂ | C₂H₅ |
| 29 | CH₂=CHCH₂ | C(CH₃)₂=CH₂CH₂CH(CH₃)CH₂CH₂ | C₂H₅ |

TABLE I-continued

[Structure: pyridine ring attached to C=C(SR)(SR¹) with C(=O)OR² group]

| Cpd. No. | R | R¹ | R² |
|---|---|---|---|
| 30 | CH₂=CHCH₂ | [1,3-dioxolan-2-yl with CH₂CH₂ substituent (O-CH(OH) cyclic)] | C₂H₅ |
| 31 | CH₂=CHCH₂ | [1,3-dioxan-2-yl with CH₂CH₂ substituent (O-CH(OH) cyclic)] | C₂H₅ |
| 32 | CH₂=CHCH₂ | CH₃OCH₂CH₂ | C₂H₅ |
| 33 | CH₂=CHCH₂ | CH(OCH₃)₂CH₂ | C₂H₅ |
| 34 | (CH₃O)₂CHCH₂ | CH₂=CHCH₂CH₂ | C₂H₅ |
| 35 | CH₃SCH₂CH₂ | CH₂=CHCH₂ | C₂H₅ |
| 36 | CH₂=CHCH₂ | N≡CCH₂CH₂ | C₂H₅ |
| 37 | CH₂=CHCH₂ | CH₃SO₂CH₂CH₂ | C₂H₅ |
| 38 | CH₃CH₂CH₂ | CH₂=CHCH₂Si(CH₃)₂CH₂ | C₂H₅ |
| 39 | CH₂=CHCH₂ | 4-CH₃O-C₆H₄-CH₂ | C₂H₅ |
| 40 | CH₂=CHCH₂ | 3,4-(CH₃O)₂-C₆H₃-CH₂ | C₂H₅ |
| 41 | CH₂=CHCH₂CH₂ | 3,4-(CH₃O)₂-C₆H₃-CH₂ | C₂H₅ |
| 42 | CH₂=CHCH₂CH₂ | 3,4-methylenedioxy-C₆H₃-CH₂ | C₂H₅ |
| 43 | CH₂=CHCH₂CH₂ | 3,4-ethylenedioxy-C₆H₃-CH₂ | C₂H₅ |
| 44 | CH₂=CHCH₂ | 3,4,5-(CH₃O)₃-C₆H₂-CH₂ | C₂H₅ |

TABLE I-continued

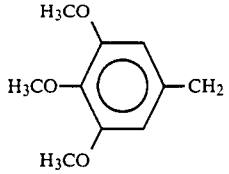

| Cpd. No. | R | R¹ | R² |
|---|---|---|---|
| 45 | $CH_2=CHCH_2CH_2$ | 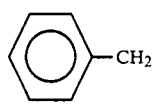 | $C_2H_5$ |
| 46 | $CH_2=CHCH_2$ | $CH_2=CHCH_2$ | $(CH_2)_4CH_3$ |
| 47 | 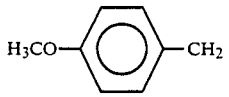 | $CH_2=CHCH_2$ | $n\text{-}C_5H_{11}$ |
| 48 | $CH_2=CHCH_2$ | 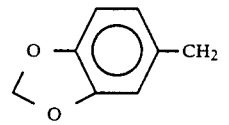 | $(CH_2)_4CH_3$ |
| 49 | $CH_2=CHCH_2$ | 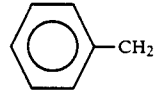 | $(CH_2)_4CH_3$ |
| 50 | $CH_2=CHCH_2$ | 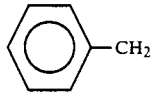 | $CH(CH_3)_2$ |
| 51 | 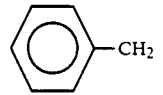 | 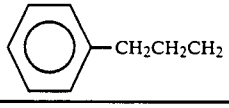 | $CH(CH_3)_2$ |
| 52 | $CH_2=CHCH_2$ | 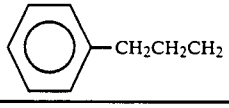 | $C_2H_5$ |

TABLE II

Nuclear Magnetic Resonance (NMR) Data
(PPM, CDCl₃)

| Cpd. No. | |
|---|---|
| 1 | t(3)1.05–1.3; m(4)3.1–3.7; q(2)3.9–4.3; m(2)7.1–7.7; m(2)8.5 |
| 2 | t(3)1.0–1.2; q(2)3.2–3.7; q(2)3.9–4.3; q(1)4.7–5.1; m(7)7.1–7.6; m(2)8.4–8.6 |
| 3 | s(3)3.5; s(2)4 0; s(2)3.8; m(13)7.4–7.8; d(1)8.5 |
| 4 | t(3)1.1–1.3; m(2)3.3–3.5; q(4)3.7–4.4; m(4)4.7–5.3; m(2)5.5–6.0; m(1)7.0–7.3; m(1)7.5–7.9; m(2)8.5–8.7 |
| 5 | t(3)1.1–1.3; m(2)4.1; m(4)4.3–4.4; m(12)7.2–7.6; m(2)8.4–8.7 |
| 6 | t(6)0.8–1.1; m(11)1.1–1.8; m(4)2.5–3.0; q(2)4.0–4.4; m(1)7.1–7.4; m(1)7.5–7.8; m(2)8.4–8.7 |
| 7 | t,t(6)1.2–1.5; s,s(3)2.35, 2.54; m(4)2.6–3.4; m(4)4.1–4.5; m(1)7.2–7.5; m(1)7.6–7.9; m(2)8.5–8.7 |
| 8 | t,t(3)1.0–1.4; m(4)3.3–4.0; m(2)4.0–4.2; m(2)4.8–5.4; m(1)5.5–6.0; m(6)7.0–7.4; m(1)7.4–7.9; m(2)8.3–8.8 |
| 9 | [t,0.9–1.1 & m,1.2–1.5(21)]; t,t(4)2.7–3.2; q(2)4.2–4.6; m(1)7.3–7.5; m(1)7.6–7.9; m(2)8.5–8.7 |
| 10 | t,t,t(9)0.8–1.4; m(4)1.5–1.9; t,t(4)2.6–3.0; q(2)4.1–4.5; m(1)7.1–7.4; m(1)7.6–7.8; m(2)8.5–8.7 |
| 11 | t,t,t(9)0.9–1.1; m(16)1.2–1.8; t,t(4)2.7–3.1; q(2)4.1–4.5; m(1)7.2–7.5; m(1)7.6–7.8; m(2)8.5–8.7 |
| 12 | t,t,t(9)1.1–1.5; q,q(4)2.6–3.1; q(2)4.0–4.5; m(1)7.1–7.4; m(1)7.6–7.8; m(2)8.4–8.6 |
| 13 | t(3)1.1–1.4; m(4)2.2–2.6; q(4)2.6–3.1; q(2)4.1–4.6; t(4)4.9–5.2; m(2)5.3–5.8; m(1)7.1–7.4; m(1)7.6–7.8; m(2)8.4–8.6 |
| 14 | t(3)1.2–1.4; s,s(6)1.85,1.6; s,s(4)34,3.6; q(2)4.1–4.5; t(4)4.8–5.2; m(1)7.1–7.4; m(1)7.5–7.8; m(2)8.5–8.7 |
| 15 | t,t(3)1.1–1.5; s,s(3)2.25–2.5; m(2)3.8–4.2; m(2)4.3–4.5; m(1)7.1–7.4; s(4)7.3; m(1)7.5–7.8; m(2)8.4–8.6 |
| 16 | t(6)0.9–1.1; m(16)1.2–1.6; q,q(2)2.9–3.1; |

TABLE II-continued

Nuclear Magnetic Resonance (NMR) Data
(PPM, CDCl₃)

| Cpd. No. | |
|---|---|
| | q,q(2)3.3–3.7; q(2)4.1–4.5; m(2)4.9–5.4; m(1)5.5–6.1; m(1)7.2–7.4; m(1)7.6–8.0; m(2)8.4–8.7 |
| 17 | t,t,t(15)0.9–1.5; m(2)1.7–2.3; q(4)2.6–3.0; q(2)4.1–4.5; m(1)7.1–7.4; m(1)7.6–7.8; m(2)8.4–8.6 |
| 18 | s(12)1.3; m(2)3.3–3.7; s,s(2)3.9–4.1; m(2)3.8–4.5; m(3)5.1–5.6; m(5)7.1–7.3; m(1)8.1–8.4; m(2)8.6–8.9 |
| 19 | t(3)1.2–1.4; s,s(4)3.8, 3.9; q(2)4.2–4.6; m(4)5.4–5.6; m(1)7.2–7.4; m(1)7.6–7.9; m(2)8.6–8.8 |
| 20 | t(3)1.1–1.4; m(4)3.3–3.8; q(2)4.1–4.5; m(4)5.7–6.5; m(1)7.2–7.5; m(1)7.6–7.9; m(2)8.6–8.7 |
| 21 | t(19)0.9–1.7; m(3)3.3–3.7; q(2)4.1–4.4; m,m(3)5.0–6.2; m(1)7.2–7.5; m(1)7.6–7.8; m(2)8.5–8.7 |
| 22 | t(3)1.1–1.3; m(2)1.7–2.2; m(4)2.4–2.9; q(2)3.2–3.6; q(2)4.0–4.4; m(3)4.9–6.0; m(6)7.0–7.3; m(1)7.4–7.6; m(2)8.3–8.6 |
| 23 | s,s(12)1.1–1.3; m(2)1.8–2.3; m(2)2.8–3.1; m(2)3.2–3.5; m(4)3.8–4.3; m,m(3)4.8–6.0; m(2)6.6–6.9; m(3)7.1–7.3; m(1)7.5–7.7; m(2)8.4–8.6 |
| 24 | t(3)1.1–1.4; s,s(12)1.6–1.9; d,d(4)3.3–3.8; q(2)4.1–4.5; t,t(2)5.0–5.5; m(1)7.1–7.4; m(1)7.6–7.8; m(2)8.5–8.7 |
| 25 | t(9)1.1–1.5; m(4)1.8–2.3; s,s(3)2.3,2.5; m(2)2.7–3.2; q(2)4.2–4.6; d,s(2)4.9–5.2; m(1)5.5–6.3; m(1)7.2–7.4; m(1)7.7–7.8; m(2)8.5–8.7 |
| 26 | t(3)1.2–1.4; m(12)1.5–2.0; m(4)3.1–3.9; t(2)4.0–4.6; s(4)4.9; m(1)7.1–7.4; m(1)7.5–8.0; m(2)8.3–8.7 |
| 27 | t,t(6)1.1–1.5; m(4)2.9–3.3; m(4)3.3–3.9; q(2)4.1–4.5; m,m(3)4.9–6.1; m(1)7.2–7.5; m(1)7.6–7.9; m(2)8.5–8.7 |
| 28 | t,t(3)1.1–1.4; m(4)3.0–3.7; m,m,(4)3.8–4.5; m,m(4)4.9–5.4; m(1)5.5–6.0; m(1)6.1–6.7; m(1)7.1–7.4; m(1)7.5–8.0; m(2)8.4–8.8 |
| 29 | m,m(19)0.9–2.9; q(4)3.1–3.9; q(2)4.0–4.4; m,m(4)4.8–6.1; m(1)7.0–7.3; m(1)7.5–7.9; m(2)8.4–8.8 |
| 30 | t,t(3)1.2–1.5; m(2)1.8–2.3; q(2)3.3–3.7; d(4)3.9–4.1; q(2)4.1–4.5; m,m(4)4.8–6.2; m(1)7.2–7.5; m(1)7.6–8.0; m(1)7.6–8.0 |
| 31 | t,t(3)1.1–1.5; m(2)1.9–2.4; q(2)2.8–3.3; m(4)3.4–4.0; m(6)4.0–4.9; m,m(4)5.0–6.2; m(1)7.2–7.5; m(1)7.7–8.1; m(2)8.5–8.9 |
| 32 | t,t(3)0.9–1.3; m,m(9)2.6–3.6; q(2)3.9–4.3; m,m(3)4.6–6.0; m(1)7.0–7.2; m(1)7.0–7.2; m(1)7.4–7.8; m(2)8.3–8.7 |
| 33 | t,t(3)1.1–1.4; m,m(12)2.7–4.6; m,m(4)4.8–6.1; m(1)7.8–8.0; m(2)8.4–8.8 |
| 34 | t(3)1.2–1.4; m,m(6)2.0–3.2; m,m(6)3.3–4.6; m(4)4.7–5.3; m(2)5.4–6.2; m(1)7.1–7.4; m(1)7.5–7.8; m(2)8.5–8.7 |
| 35 | t,t(3)1.1–1.4; s,s(3)2.05,2.15; m,m(6)2.4–3.9; q(2)4.0–4.4; m,m(3)4.8–6.1; m(1)7.1–7.4; m(1)7.5–8.0; m(2)8.4–8.8; |
| 36 | t,t(3)1.1–1.4; q(2)2.5–3.0; q,q(4)3.0–3.9; q(2)4.0–4.4; m,m(3)4.8–6.1; ,(1)7.1–7.4; m(1)7.5–8.0; m(2)8.4–8.8 |
| 37 | t(3)1.1–1.3; s(3)3.0; m,m(6)3.3–3.9; q(2)4.0–4.4; m,m(3)4.9–6.0; m(1)7.1–7.4; m(1)7.6–8.0; m(2)8.4–8.8 |
| 38 | s,s(6)0.1–0.5; m,m(10)0.9–1.8; m(2)2.0–2.5; m(2)2.6–3.0; q(2)4.1–4.5; m(2)4.7–5.1; m(1)7.2–7.5; m(1)7.6–7.9; m(2)8.5–8.7 |
| 39 | t,t(3)1.1–1.4; m(2)3.5–3.9; s(3)3.8; m,m(4)4.0–4.7; m,m(2)4.9–5.5; m(1)5.6–6.1; m,m(5)6.7–7.5; m(1)7.5–8.1; m(2)8.4–8.9 |
| 52 | t(3)1.1–1.3; ;m(2)1.7–2.2; m(4)2.4–2.9; q(2)3.2–3.6, q(2)4.0–4.4, m(3)4.9–6.0; m(6)7.0–7.3; m(1)7.4–7.6; m(2)8.3–8.6 |

EXAMPLE 5

Preparation of Fungicidal Compositions

The compounds prepared in Examples 1-3 (Compound Nos. 1-52) were formed into compositions. This was accomplished by dissolving 0.3 grams of each of the compounds in 10 ml of acetone or other suitable solvent. Each of these solutions were treated with 1 to 2 drops of an emulsifying agent, such as Triton [trademark] X-100, and water was added to form an emulsion. The degree of dilution with water was dictated by the desired concentration of the composition. The greater the quantity of water added, the lower the concentration of the composition, reported in milligrams per liter (mg/l).

EXAMPLE 6

Control of Powdery Mildew Fungus (Systemic Root Uptake)

Compound Nos 1-52 were tested to evaluate their effectiveness in preventing or controlling powdery mildew disease of barley caused by the fungus *Erysiphe graminis* and powdery mildew disease of cucumber caused by the fungus, *Erysiphe cichoracearum*. This prevention or control capability was tested by utilizing the compounds to control these diseases by systemic root uptake.

Ten plants of barley (Variety "Herta") and cucumber (Variety "Marketmore 70") were grown in pots (4×4×3.5 inches) to age 6 days and 10 days, respectively. Upon reaching these ages, 45 ml of emulsion compositions formed in accordance with Example 5 were added to each pot. That is, 52 pots were treated with emulsion compositions of the 52 compounds prepared in accordance with Examples 1-3. The 45 ml compositions saturated the soil without significant loss through drainage into the saucers below the pots. In addition, a number of control pots containing the same barley and cucumber plants were left untreated.

Twenty-four hours after the treatment with the compositions of the present invention, both the treated and untreated barley and cucumber plants were inoculated with powdery mildew fungus. This was accomplished by tapping leaves of previously infected barley and cucumber plants over the treated and untreated pots containing the barley and cucumber plants, respectively, to distribute spores of the fungus over the plants tested.

Six days after inoculation, disease control was evaluated on a 0 to 6 rating scale. A 0 rating was assigned when no disease was evidenced and 6 rating was given for severe disease. Intermediate ratings were assigned depending on the degree of disease. Percent control was computed by comparing the ratings of the treated and untreated plants.

The percent control for each of the compounds tested is reported in Table III. The results of the powdery mildew disease control of barley is reported under the title of "BMS 250", and for powdery mildew disease of cucumber under "CMS 250". It is noted that Table III appears after Example 12.

EXAMPLE 7

Control of Powdery Mildew in Barley by Foliar Application

Eight plants of "Larker" variety barley were planted in a pot. The number of pots were sufficient to accommodate testing in duplicate or triplicate pots for each of the 52 compounds tabulated in Table I. This number included a duplicate number of pots which acted as controls as will be discussed below.

Each of the compounds tabulated in Table I were tested by being sprayed onto the plants as a composition, prepared in accordance with Example 5 at an emulsion composition concentration of 1,000 mg/l. Compositions of each compound were sprayed on two or three pots. A number of pots were unsprayed and thus acted as controls. That is, for each pot sprayed an unsprayed pot was utilized as a control.

After the leaves of the sprayed pots were dried, they and the unsprayed control pots were placed in a greenhouse maintained at 21° C. All the pots were then inoculated with barley powdery mildew fungus, *Erysiphe graminis*. This inoculation was accomplished by distributing spores of the fungus over the leaves to be tested from plants which had previously been infected with the mildew disease.

Five days after inoculation, the plants were evaluated and assigned a disease rating of 0 to 6 as described in Example 6. Again, percent control was computed by comparing the treatment scores with the scores of the untreated controls. The results of these tests are summarized in Table III under the title "BMP 1000".

EXAMPLE 8

Control of Rice Blast Disease by Foliar Treatment

Five Bellemont rice plants were grown in each of several pots. The number of pots with planted rice plants were sufficient to test the compositions of all compounds listed in Table I as well as controls therefor, the number of controls equal to the number of pots treated with each compound.

Three to four weeks after planting, the rice plants were sprayed with compositions of the compounds of this invention, prepared in accordance with Example 5. The concentration of each composition was 1,000 mg/l. An equal number of pots, also containing five rice plants per pot, remained unsprayed.

Sprayed and unsprayed pots of the plant were inoculated with spores of the rice blast fungus, *Pyricularia oryzae*. This inoculation was accomplished by preparing inoculum containing 20,000 to 30,000 spores per milliliter. The inoculum so prepared was sprayed on the plants with 1 to 2 drops of Tween [trademark] 20 surfactant (ethoxylated sorbitan monolaurate) to assure proper wetting of the inoculum onto the plant leaves.

The plants were incubated in a controlled environmental chamber at a humidity of 99% and a temperature of 21° C. for about 24 hours to allow infection to occur. The plants, after 24 hours in the control chamber, were transferred to a greenhouse for six days to permit disease development to occur. Disease was manifested by blast lesions on the leaves. Disease control was calculated by either counting lesions, if infection was moderate, or evaluating by the 0 to 6 rating system defined in Example 6. The results of this test are also tabulated in Table III under the title "RCB 1000".

EXAMPLE 9

Control of Bean Rust Fungus Eradicant Test

Pots were planted with two pinto bean plants, *P. vulgaris* each, susceptible to rust disease. When the plants were 7 days old, at the primary leaf stage of growth, they were all sprayed with a suspension containing 20,000 spores of the bean rust fungus, *Uromyces phaseoli*, per ml. All the pots containing the plants were then incubated in a controlled environmental chamber, maintained at 99% humidity and 21° C., for 24 hours to allow infection to occur. The plants were then removed from the incubator and allowed to dry. Two days after inoculation the infected plants were sprayed with compositions formed from the compounds of this invention at a dosage of 1,000 mg/l. A number of infected plants were not sprayed and acted as controls. All of the sprayed and unsprayed plants were then placed in a greenhouse at 21° C. for five days to allow any disease present to be expressed.

All the plants sprayed with the spore suspension were assessed for disease using the 0 to 6 rating system described in Example 6. Control of disease was determined by comparing treated plants with the untreated controls. The control of disease, expressed as percent reduction of disease, is included in Table III under the title "BRE 1000".

EXAMPLE 10

Control of Peanut Cercospora Leafspot by Foliar Treatment

Four Virginia peanut plants were grown in each of several pots. Enough pots were prepared so that the four plants in each of the pots could be sprayed with each of the compounds listed in Table I. This spraying occurred when the plants reached 4 weeks old. The 52 compounds of this invention were applied to the peanut plants by spraying emulsion compositions, prepared in accordance with the method employed in Example 5. The concentration of the emulsion compositions were 900 mg/l for each of the compounds listed in Table I. A number of pots containing four 4-week old Virginia peanut plants were left untreated to act as controls.

The treated (sprayed) and control (unsprayed) plants, after drying, were inoculated with spores of Peanut Cercospora leafspot, *Cercospora arachidicola*. The inoculum contained 20,000 to 30,000 spores per ml. The inoculum was sprayed with 1 to 2 drops of Tween [trademark] 20 surfactant (ethoxylated sorbitan monolaurate) to aid in wetting the leaves with the inoculum. All the inoculated peanut plant pots were incubated in a temperature-humidity control chamber at 24° C. for 36 hours to develop infection. The plants were then placed in a greenhouse for 21 days to allow disease development.

After 21 days in the greenhouse, all the plants were evaluated on the 0 to 6 disease rating system. Percent control was computed by comparing the scores of the treated pots and the untreated control pots. The results of this test are summarized in Table III under the title "PNT 900".

EXAMPLE 11

Control of Barley Blast

Pots were prepared such that they included 10 plants of 6 day old barley "Herta" variety. These pots were sprayed with compositions, formulated in accordance with the procedure of Example 5 of the compounds set forth in Table I. These pots, and a number of control pots planted with 10 "Herta" variety barley plants which were unsprayed, were inoculated with spores of the blast fungus, *Pyricularia oryzae*. In that *Pyricularia oryzae* is the same fungus utilized in Example 8, the method of inoculation was in accordance with the description given in that example.

All the inoculated pots were placed in a greenhouse maintained at a temperature of 21° C. and a humidity of 99% using the 0 to 6 disease rating scale. Percent control was computed by comparing the treatment scores of the treated and untreated pots. The results of this test are included in Table III under the title "BBL 1000".

EXAMPLE 12

Control of Nine Fungus Species

Compounds listed in Table I were solubilized in acetone at a concentration of 500 mg/l. That is, solutions were made of the compounds of the present invention such that there were 500 parts by weight of active compound per million parts by volume of acetone for all fungus species. Filter paper discs, each 11 mm. diamater, were dipped in each of the test solutions. The discs were allowed to air dry to drive off the acetone solvent. A number of discs were untreated to provide controls.

The treated and untreated discs were then placed on agar plates and 7 fungus species: *Alternaria solani* (ALT), *Botrytis cinerea* (BOT), *Fusarium oxysporm* (FUS), *Helminthosporium maydis* (HMAY), *Phytophthora infestans* (PHY), *Sclerotinia sclerotiorum* (SCM) and *Sclerotium rolfsii* (SCO) were added to the center of each test disc in the form of a culture plug with the fungus mat in contact with the treated paper of the test disc. Two drops of an eighth fungi species, *Cercospora arachidicola* (CER), were added as a spore suspension (20,000 spores/ml) to the chemically treated test disc, rather than a mycelial culture plug. The plates were incubated at 29° C. in an oven and then the eight fungus species were evaluated by measuring the radius from the center of the fungus colony of the untreated discs.

Percent growth inhibition of each of the compounds tested was determined as a function of the difference between the radii of the treated and untreated disc for the eight fungus species.

In the case of the *Cercospora arachidicola* (CER) fungi, scoring was done on a numerical basis as follows:

100=Complete inhibition of germination and growth.

80=Nearly complete inhibition but some growth.

50=Partial inhibition of growth or, early complete inhibition but later growth begins.

20=Some inhibition of growth, but not significant.

0=No inhibition of growth.

The results of all the above tests appear in Table III under the titles "ALT 500", "BOT 500", "FUS 500", "HMAY 500", "PHY 500", "SCM 500", "SCO 500" and "CER 500".

TABLE III

| | | | | | | Percent Fungicidal Control | | | | | | | | |
|---|---|---|---|---|---|---|---|---|---|---|---|---|---|---|
| Cpd. No. | ALT 500 | BBL 1000 | BMP 1000 | BMS 250 | BOT 500 | BRE 1000 | CER 500 | CMS 250 | FUS 500 | HMAY 500 | PHY 500 | PNT 900 | RCB 1000 | SCM 500 | SCO 500 |
| 1 | 0 | 0 | 60 | 15 | 15 | 0 | 0 | 40 | 10 | 20 | 60 | — | — | 0 | 45 |
| 2 | 40 | 85 | 100 | 0 | 0 | 0 | 35 | 0 | 60 | 30 | 75 | — | — | 45 | 25 |
| 3 | 0 | 85 | 15 | 15 | 0 | 0 | 0 | 40 | 0 | 40 | 0 | — | — | 15 | 25 |
| 4 | 65 | 100 | 100 | 15 | 100 | 0 | 100 | 0 | 70 | 100 | 100 | 9 | — | 0 | 100 |
| 5 | 20 | 90 | 100 | 15 | 0 | 0 | 0 | 0 | 10 | 20 | 0 | — | — | 0 | 0 |
| 6 | 0 | 60 | 20 | 65 | 10 | 0 | 0 | 0 | 0 | 60 | 0 | — | — | 0 | 94 |
| 7 | 0 | 0 | 50 | 35 | 0 | 0 | 0 | 0 | 0 | 0 | 40 | — | — | 25 | 0 |
| 8 | 65 | 90 | 100 | 35 | 100 | 0 | 100 | 15 | 60 | 100 | 100 | 8 | 50 | 0 | 100 |
| 9 | 0 | 85 | 100 | 15 | 0 | 0 | 0 | 35 | 0 | 0 | 0 | — | — | 0 | 0 |
| 10 | 0 | 0 | 60 | 6 | 5 | 0 | 0 | 15 | 0 | 15 | 60 | — | — | 0 | 10 |
| 11 | 0 | 0 | 0 | 0 | 5 | 0 | 0 | 35 | 0 | 0 | 0 | — | — | 25 | 0 |
| 12 | 25 | 15 | 80 | 0 | 96 | 0 | 0 | 65 | 15 | 20 | 100 | — | — | 15 | 40 |
| 13 | 0 | 100 | 100 | 15 | 30 | 0 | 0 | 15 | 10 | 40 | 60 | — | 29 | 0 | 25 |
| 14 | 20 | 90 | 100 | 0 | 100 | 50 | 0 | 15 | 10 | 55 | 100 | — | — | 35 | 100 |
| 15 | 35 | 100 | 100 | 0 | 35 | 50 | 0 | 20 | 0 | 35 | 60 | — | — | 0 | 15 |
| 16 | 10 | 90 | 100 | 15 | 65 | 0 | 0 | 15 | 10 | 65 | 95 | — | — | 20 | 75 |
| 17 | 0 | 35 | 50 | 50 | 0 | 0 | 0 | 15 | 0 | 35 | 60 | — | — | 0 | 0 |
| 18 | 20 | 90 | 100 | 15 | 45 | 0 | 25 | 35 | 50 | 40 | 100 | — | — | 0 | 35 |
| 19 | 20 | 90 | 100 | 15 | 35 | 0 | 0 | 15 | 15 | 75 | 88 | — | — | 50 | 0 |
| 20 | 45 | 0 | 0 | 15 | 0 | 0 | 100 | 15 | 0 | 30 | 65 | 0 | — | 30 | 80 |
| 21 | 0 | 90 | 100 | 0 | 70 | 0 | 50 | 0 | 0 | 65 | 0 | — | — | 0 | 35 |
| 22 | 50 | 90 | 100 | 0 | 100 | 0 | 100 | 0 | 12 | 100 | 97 | 100 | 67 | 0 | 75 |
| 23 | 0 | 0 | 100 | 0 | 20 | 0 | 0 | 0 | 0 | 35 | 0 | — | — | 0 | 0 |
| 24 | 0 | 0 | 100 | 20 | 0 | 0 | 0 | 20 | 0 | 0 | 50 | — | — | 0 | 0 |
| 25 | 35 | 0 | 0 | 65 | 60 | 0 | 25 | 0 | 20 | 70 | 72 | — | — | 0 | 70 |
| 26 | 35 | 0 | 60 | 0 | 80 | 0 | 0 | 0 | 5 | 10 | 50 | — | — | 54 | 100 |
| 27 | 60 | 65 | 60 | 0 | 100 | 0 | 100 | 0 | 5 | 75 | 35 | 17 | 4 | 65 | 100 |
| 28 | 60 | 0 | 90 | 15 | 100 | 0 | 100 | 0 | 20 | 75 | 40 | 17 | — | 60 | 100 |
| 29 | 35 | 0 | 0 | 0 | 100 | 0 | 100 | 15 | 30 | 50 | 100 | 0 | — | 25 | 100 |
| 30 | 35 | 15 | 40 | 0 | 100 | 0 | 100 | 15 | 35 | 45 | 100 | 0 | — | 27 | 100 |
| 31 | 20 | 15 | 20 | 0 | 100 | 0 | 100 | 35 | 30 | 50 | 100 | 0 | — | 5 | 100 |
| 32 | 35 | 0 | 0 | 0 | 100 | 0 | 100 | 15 | 45 | 87 | 100 | 25 | — | 30 | 100 |
| 33 | 45 | 0 | 0 | 0 | 0 | 0 | 75 | 0 | 50 | 80 | 100 | 8 | — | 25 | 100 |
| 34 | 0 | 0 | 0 | 0 | 40 | 0 | 0 | 0 | 35 | 85 | 60 | — | — | 55 | 66 |
| 35 | 45 | 0 | 15 | 65 | 92 | 0 | 100 | 0 | 45 | 40 | 100 | 0 | — | 0 | 50 |
| 36 | 16 | 90 | 100 | 50 | 55 | 0 | 25 | 0 | 55 | 61 | 100 | — | — | 12 | 67 |
| 37 | 0 | 0 | 90 | 0 | 25 | 0 | 0 | 0 | 15 | 0 | 50 | — | — | 0 | 65 |
| 38 | 0 | 100 | 90 | 15 | 0 | 0 | 0 | 0 | 0 | 0 | 80 | — | — | 25 | 20 |
| 39 | 90 | 100 | 100 | 0 | 65 | 0 | 100 | 15 | 15 | 75 | 85 | — | 50 | 45 | 100 |
| 40 | 35 | 90 | 90 | 0 | 65 | 0 | 75 | 0 | 35 | 75 | 75 | — | — | 0 | 100 |
| 41 | 75 | 85 | 20 | 0 | 35 | 0 | 0 | 0 | 0 | 35 | 70 | — | — | 0 | 25 |
| 42 | 100 | 90 | 90 | 0 | 65 | 0 | 100 | 0 | 50 | 100 | 10 | — | — | 0 | 100 |
| 43 | 0 | 100 | 90 | 15 | 0 | 0 | 0 | 15 | 15 | 65 | 0 | — | — | 0 | 0 |
| 44 | 35 | 90 | 90 | 0 | 35 | 0 | 100 | 0 | 50 | 75 | 0 | — | — | 25 | 70 |
| 45 | 0 | 85 | 65 | 0 | 0 | 0 | 0 | 0 | 15 | 15 | 0 | — | — | 0 | 0 |
| 46 | 0 | 90 | 100 | 0 | 35 | 0 | 75 | 0 | 0 | 60 | 87 | — | — | 0 | 0 |
| 47 | 0 | 85 | 90 | 0 | 35 | 0 | 0 | 0 | 0 | 30 | 75 | — | — | 0 | 0 |
| 48 | 25 | 50 | 90 | 0 | 0 | 0 | 0 | 15 | 0 | 20 | 80 | — | — | 0 | 20 |
| 49 | 0 | 15 | 90 | 0 | 0 | 0 | 75 | 0 | 15 | 70 | 85 | — | — | 20 | 80 |
| 50 | 50 | 90 | 100 | 0 | 35 | 100 | 50 | 35 | 15 | 75 | 95 | — | — | 20 | 100 |
| 51 | 0 | 0 | 80 | 20 | 0 | 0 | 0 | 15 | 0 | 0 | 10 | — | — | 0 | 0 |

TABLE III-continued

| Cpd. No. | ALT 500 | BBL 1000 | BMP 1000 | BMS 250 | BOT 500 | BRE 1000 | CER 500 | CMS 250 | FUS 500 | HMAY 500 | PHY 500 | PNT 900 | RCB 1000 | SCM 500 | SCO 500 |
|---|---|---|---|---|---|---|---|---|---|---|---|---|---|---|---|
| | | | | | | | Percent Fungicidal Control | | | | | | | | |
| 52 | 0 | 100 | 100 | 0 | 0 | 0 | 50 | 0 | 0 | 100 | 100 | — | — | 0 | 15 |

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, this invention should be limited only by the appended claims.

We claim:

1. A compound of the formula

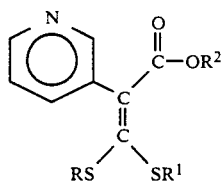

wherein;

R and $R^1$ are each independently members selected from the group consisting of
$C_1$-$C_{10}$ alkyl,
$C_1$-$C_{10}$ cyanoalkyl,
$C_7$-$C_{13}$ arylalkyl,
$C_2$-$C_9$ alkenyl,
$C_3$-$C_9$ haloalkenyl
$C_3$-$C_{10}$ alkoxyalkyl,
$C_3$-$C_{10}$ alkylthioalkyl,
$C_3$-$C_{10}$ alkylsulfonylalkyl,
$C_3$-$C_8$ carbalkoxyalkyl,
$C_4$-$C_{10}$ alkylenedioxyalkyl,
$C_7$-$C_{13}$ aryloxyalkyl, and
$C_5$-$C_8$ alkenyloxyalkyl; and
$R^2$ is $C_1$-$C_5$ alkyl.

2. A compound in accordance with claim 1 wherein R and $R^1$ are each independently a substituent or group of substituents representing
$C_1$-$C_{10}$ alkyl, benzyl, 4-chlorobenzyl, 4-methoxybenzyl, 4-t-butylbenzyl, 3,4-dimethylbenzyl, 3,4,5-trimethoxybenzyl, 3,4-methylenedioxybenzyl, 2-vinyloxyethyl, 2,2-dimethoxyethyl, 2-methoxyethyl, 2-(methylthio)ethyl, 2-(1,3-dioxolan-2-yl)ethyl, 2-(1,3-dioxolan-2-yl)ethyl, carboethoxymethyl, 2-carboethoxyethyl, 2-cyanoethyl, 3-phenoxypropyl, 3-(4-t-butylphenoxy)propyl, 2-methylallyl, 3,3-dimethylallyl, but-3-en-1-yl, 3,7-dimethyloct-6-en-1-yl, 2-chloroallyl or 3-chloroallyl, and
$R^2$ is methyl, ethyl, isopropyl or n-pentyl.

3. A compound in accordance with claim 1 wherein the compound is ethyl 3,3-bis(allylthio)-2-(3-pyridyl)acrylate.

4. A compound in accordance with claim 1 wherein the compound is selected from the group consisting of the cis or trans isomer, or a mixture thereof, of ethyl 3-allylthio-3-benzylthio-2-(3-pyridyl)acrylate.

5. A compound in accordance with claim 1 wherein the compound is ethyl 3,3-bis(2-methyl-2-propenylthio)-2-(3-pyridyl)acrylate.

6. A compound in accordance with claim 1 wherein the compound is selected from the group consisting of the cis or trans isomer, or a mixture thereof, of ethyl 3-(allylthio)-3-(3-phenoxypropylthio)-2-(3-pyridyl)acrylate.

7. A compound in accordance with claim 1 wherein the compound is selected from the group consisting of the cis or trans isomer, or a mixture thereof, of ethyl 3-(allylthio-3-(3,7-dimethyloct-6-en-1-yl-thio)-2-(3-pyridyl)acrylate.

8. A compound in accordance with claim 1 wherein the compound is selected from the group consisting of the cis or trans isomer, or a mixture thereof, of ethyl 3-allylthio-3-[2-(1,3-dioxolan-2-yl)ethylthio]-2-(3-pyridyl) acrylate.

9. A compound in accordance with claim 1 wherein the compound is selected from the group consisting of the cis or trans isomer, or a mixture thereof, of ethyl 3-allylthio-3-(2-methoxyethylthio)-2-(3-pyridyl)acrylate.

10. A compound in accordance with claim 1 wherein the compound is selected from the group consisting of the cis or trans isomer, or a mixture thereof, of ethyl 3-allylthio-3-(4-methoxybenzylthio)-2-(3-pyridyl)acrylate.

11. A compound in accordance with claim 1 wherein the compound is selected from the group consisting of the cis or trans isomer, or a mixture thereof, of ethyl 3-allylthio-3-(1,3-benzodioxol-5-yl-methylthio)-2-(3-pyridyl)acrylate.

12. A fungicidal composition comprising A) a fungicidally effective amount of a compound of claim 1, and B) an agriculturally acceptable carrier.

13. A method for controlling phytopathogenic fungi comprising applying a fungicidally effective amount of a compound according to claim 1 to a locus to be protected.

14. A method according to claim 13 wherein the compound is applied to plant foliage.

15. A method according to claim 13 wherein the compound is applied to soil.

* * * * *